United States Patent
Arifuku et al.

(10) Patent No.: US 12,195,436 B2
(45) Date of Patent: *Jan. 14, 2025

(54) METHOD FOR DECOMPOSING FLAVONOID GLYCOSIDE AND METHOD FOR PRODUCING FLAVONOID

(71) Applicant: Showa Denko Materials Co., Ltd., Tokyo (JP)

(72) Inventors: Motohiro Arifuku, Tokyo (JP); Yoshiaki Kurihara, Tokyo (JP); Masato Kaneeda, Tokyo (JP)

(73) Assignee: RESONAC CORPORATION, Tokyo (JP)

( * ) Notice: Subject to any disclaimer, the term of this patent is extended or adjusted under 35 U.S.C. 154(b) by 485 days.

This patent is subject to a terminal disclaimer.

(21) Appl. No.: 17/262,207

(22) PCT Filed: Jul. 26, 2019

(86) PCT No.: PCT/JP2019/029527
§ 371 (c)(1),
(2) Date: Jan. 22, 2021

(87) PCT Pub. No.: WO2020/022509
PCT Pub. Date: Jan. 30, 2020

(65) Prior Publication Data
US 2021/0292294 A1    Sep. 23, 2021

(51) Int. Cl.
*C07D 311/40*    (2006.01)

(52) U.S. Cl.
CPC .................. *C07D 311/40* (2013.01)

(58) Field of Classification Search
CPC .................................... C07D 311/40
See application file for complete search history.

(56) References Cited

FOREIGN PATENT DOCUMENTS

| CN | 101357912 | | 2/2009 |
|----|-----------|---|--------|
| CN | 101715445 | | 5/2010 |
| CN | 107501224 | * | 12/2017 |
| JP | 2005145824 | | 6/2005 |
| JP | 2008208064 | A * | 9/2008 |
| WO | 2008155890 | | 12/2008 |

OTHER PUBLICATIONS

Wenzel et al. Food Sci Nutr. Nov. 2015; 3(6): 569-576.*
Kim et al. (Separation Science and Technology, 44:2598-2608, 2009).*
Hoshino (Trans. Mat. Res. Soc. Japan 39[3] 309-311 (2014)).*
Nakayama Tsutomu—JP 2011153084-PD Aug. 11, 2011—Google patents translation.*
Duangkamol Ruen-Ngam, et al., "Hydrothermal Hydrolysis of Hesperidin Into More Valuable Compounds Under Supercritical Carbon Dioxide Condition," Industrial & Engineering Chemistry Research, vol. 51, Oct. 2012, pp. 13545-13551.
Masao Tsukayama, et al., "Microwave-Assisted Extraction and Methylation of Useful Flavones from Waste Peels of Citrus sudachi," Nippon Shokuhin Kagaku Kogaku Kaishi, vol. 57, Oct. 2010, pp. 427-433.

* cited by examiner

*Primary Examiner* — Valerie Rodriguez-Garcia
(74) *Attorney, Agent, or Firm* — JCIPRNET

(57) ABSTRACT

Provided is a method for decomposing a flavonoid glycoside, wherein a flavonoid glycoside is decomposed into a flavonoid by heat-treating a flavonoid glycoside-containing raw material in the presence of an alcohol in a sealed container at a temperature exceeding the boiling point of the alcohol under atmospheric pressure.

9 Claims, No Drawings

METHOD FOR DECOMPOSING FLAVONOID GLYCOSIDE AND METHOD FOR PRODUCING FLAVONOID

CROSS-REFERENCE TO RELATED APPLICATION

This application is a 371 application of the International PCT application serial no. PCT/JP2019/029527, filed on Jul. 26, 2019, which claims the priority benefit of International PCT application serial no. PCT/JP2018/028287, filed on Jul. 27, 2018. The entirety of each of the above-mentioned patent applications is hereby incorporated by reference herein and made a part of this specification.

TECHNICAL FIELD

The present invention relates to a method for decomposing flavonoid glycosides and a method for producing flavonoids.

BACKGROUND ART

Flavonoids are a group of naturally occurring organic compounds, and are contained in flowers, leaves, roots, stems, fruits, seeds and the like of various plants including citrus fruits and beans. Flavonoids have different characteristics and actions depending on the type, but most of them have a strong antioxidant action. For example, polymethoxyflavone, which is a flavonoid contained in citrus fruits, is known to have an antioxidant action, a carcinogenic inhibitory action, an antibacterial action, an antiviral action, an antiallergic action, a melanin production inhibitory action, a blood glucose level inhibitory action, and the like, and is expected to be applied to various applications such as pharmaceuticals, health foods, and cosmetics.

Regarding a method for producing flavonoids from citrus fruits, for example, a method for extracting flavonoids in an aqueous ethanol solution from the pericarp of citrus fruits and the like and collecting the extracted flavonoids from the solution is known (for example, refer to Patent Literature 1).

CITATION LIST

Patent Literature

[Patent Literature 1]
Japanese Patent Laid-Open No. 2005-145824

SUMMARY OF INVENTION

Technical Problem

However, the conventional method for producing flavonoids has a problem of the yield of flavonoids being low. Therefore, it is required to develop a production method through which it is possible to improve the yield of flavonoids.

For example, the pericarp of citrus fruits contains a larger amount of flavonoid glycosides than flavonoids, but if this can be collected as flavonoids, the yield of flavonoids can be improved. Examples of a method for decomposing flavonoid glycosides into flavonoids include a method for reacting flavonoid glycosides with an acid such as hydrochloric acid. However, this method has problems that a used acid may remain and be mixed into the product and a side reaction product of the acid and flavonoids may be produced. Examples of a method for removing impurities such as an acid and byproducts include a method for separating and purifying flavonoids in the decomposition product by liquid chromatography, but this method has problems of high cost and poor production efficiency. Therefore, there is a need for a new method for decomposing flavonoid glycosides, which does not use an acid.

The present invention has been made in view of the above problems in the related art, and an objective of the present invention is to provide a method for decomposing flavonoid glycosides through which it is possible to efficiently decompose flavonoid glycosides into flavonoids without using an acid and a method for producing flavonoids through which it is possible to improve the yield of flavonoids.

Solution to Problem

In order to achieve the above objective, the present invention provides a method for decomposing flavonoid glycosides including performing a heat treatment on a raw material containing flavonoid glycosides in a sealed container in the presence of an alcohol at a temperature exceeding a boiling point of the alcohol at atmospheric pressure to decompose the flavonoid glycosides into flavonoids.

According to the method, it is possible to efficiently decompose flavonoid glycosides into flavonoid without using an acid. Here, since flavonoid glycosides are decomposed by hydrolysis, it is generally considered that they are decomposed by a hydrothermal treatment using water. However, although the reason for this is unknown, the inventors found that, when an alcohol is used in place of water, decomposition of flavonoid glycosides is promoted, and flavonoids with a high concentration are obtained. Therefore, it is possible to produce flavonoid at low cost efficiently using the method.

In the method, the flavonoid glycosides may contain sudachitin glycosides and/or demethoxysudachitin glycosides. According to the method, sudachitin glycosides and demethoxysudachitin glycosides can be decomposed particularly efficiently.

In the method, the temperature of the heat treatment may be in a range of 110 to 300° C. When the temperature is within the above range, it is possible to further promote decomposition of the flavonoid glycosides.

The present invention also provides a method for producing flavonoids including a decomposition process in which flavonoid glycosides are decomposed by the method of the present invention and an extraction process in which flavonoids are extracted from a decomposition product obtained in the decomposition process. According to this production method, it is possible to produce flavonoids in a high yield, at low cost, and efficiently.

Advantageous Effects of Invention

According to the present invention, it is possible to provide a method for decomposing flavonoid glycosides through which it is possible to efficiently decompose flavonoid glycosides into flavonoids without using an acid and a method for producing flavonoids through which it is possible to improve the yield of flavonoids.

DESCRIPTION OF EMBODIMENTS

The present invention will be described below in detail with reference to preferable embodiments. However, the present invention is not limited to the following embodiments.

In this specification, when a numerical range is indicated using "to," it means that numerical values stated before and after "to" are included as a minimum value and a maximum value. In the numerical ranges described stepwise in this specification, an upper limit value or a lower limit value described in the numerical range in a certain step can be arbitrarily combined with an upper limit value or a lower limit value described in the numerical range in another step. In the numerical ranges described in this specification, the upper limit value or the lower limit value of the numerical range may be replaced with values shown in examples. The term "A or B" may include either or both of A and B. Unless otherwise specified, materials exemplified in this specification may be used alone or two or more thereof may be used in combination.

(Method for Decomposing Flavonoid Glycosides)

A method for decomposing flavonoid glycosides according to the present embodiment is a method including performing a heat treatment on a raw material containing flavonoid glycoside in a sealed container in the presence of an alcohol at a temperature exceeding a boiling point of the alcohol at atmospheric pressure to decompose the flavonoid glycosides into flavonoids. Here, in the present embodiment, normal pressure means 0.1 MPa (atmospheric pressure).

Flavonoid glycosides are hydrophilic compounds having a structure in which flavonoids and sugars are linked by glycoside bonds. Flavonoids (aglycones), which are a source of flavonoid glycosides, are aromatic compounds having a phenylchromane framework as a basic structure, and examples thereof include flavones, flavonols, flavanones, flavanonols, isoflavones, anthocyanins, flavanols, chalcones, and aurones. Among these, the flavonoid may be polymethoxyflavone, which is a flavone.

Examples of polymethoxyflavones include sudachitin, demethoxysudachitin, nobiletin, tangeretin, pentamethoxyflavone, tetramethoxyflavone, and heptamethoxyflavone. Among these, the polymethoxyflavone may be sudachitin or demethoxysudachitin.

In addition, flavonoids may include quercetin, hesperetin, or anthocyanidin.

Sugars that are a source of flavonoid glycosides are not particularly limited, and examples thereof include known sugars that can be linked to the above flavonoids by glycoside bonds to form glycosides.

The raw material to be subjected to the heat treatment may contain components other than flavonoid glycosides. Examples of other components include flavonoids, water-soluble dietary fibers, slowly soluble dietary fibers, and sugars. The content of the flavonoid glycosides in the raw material with respect to a total amount of the solid content in the raw material is preferably 0.1 mass % or more, more preferably 0.25 to 30 mass %, still more preferably 0.3 to 15 mass %, and particularly preferably 0.5 to 5 mass %. When the raw material further contains flavonoids, the content of the flavonoid glycosides with respect to 1 part by mass of the content of the flavonoids is preferably 0.25 parts by mass or more, more preferably 0.5 to 100 parts by mass, and still more preferably 5 to 50 parts by mass.

Specifically, flowers, leaves, roots, stems, fruits, seeds, and the like of plants and seaweeds can be used as raw materials. In particular, since the pericarp contains a large amount of polymethoxyflavone and their glycosides, the squeezed residue of citrus fruits can be preferably used. In addition, the raw material may be a dry powder obtained from citrus fruits or a dry powder obtained from the pericarp of citrus fruits. Examples of citrus fruits include citrus sudachi, citrus unshiu, citrus poonensis, and citrus depressa.

The citrus fruits may be citrus sudachi containing a large amount of polymethoxyflavones such as sudachitin and demethoxysudachitin, and their glycosides.

The heat treatment can be performed by putting the raw material into a pressure-resistant sealed container together with a solvent containing an alcohol, and performing heat treatment at a temperature exceeding a boiling point of the alcohol at atmospheric pressure in the sealed state. When the reaction solution containing the raw material and the solvent is heated in the sealed container, the inside of the sealed container has a heated and pressurized environment, and a decomposition reaction of flavonoid glycosides will occur. The heat treatment may be performed while stirring the reaction solution. The pressure-resistant sealed container is not particularly limited, and for example, a known container that can be used for a hydrothermal treatment using water as a solvent can be used. Regarding the pressure-resistant sealed container, for example, an autoclave can be used.

Regarding the solvent, an alcohol may be used alone, or a mixed solvent in which an alcohol and another solvent are mixed may be used. Examples of alcohols include methanol, ethanol, propanol, and glycerin. Among these, methanol and ethanol are preferable because it is possible to further promote decomposition of flavonoid glycosides. Examples of other solvents include water, ethyl acetate, hexane, and acetone.

The solvent may be a mixed solvent of water and an alcohol. When a mixed solvent of water and an alcohol is used, a mass ratio of water to an alcohol (water/alcohol) can be 1/99 to 99/1, and can be appropriately selected depending on the solubility of glycosides to be decomposed. When a mixing ratio with high solubility is selected, the reaction can be performed more efficiently at one time. The mass ratio of water to an alcohol (water/alcohol) in the solvent may be 1/99 to 50/50, 1/99 to 20/80, 1/99 to 10/90, 2/98 to 6/94, or 3/97 to 5/95. When the mass ratio of water to an alcohol is within the above range, it is possible to further promote decomposition of flavonoid glycosides.

The content of the alcohol in the solvent with respect to a total amount of the solvent may be 50 mass % or more, 80 mass % or more, 90 mass % or more, 94 mass % or more, or 95 mass % or more and may be less than 100 mass %, 99 mass % or less, 98 mass % or less, or 97 mass % or less. When the content of the alcohol in the solvent is equal to or larger than the lower limit value, and it is possible to further promote decomposition of flavonoid glycosides.

The content of water in the solvent with respect to a total amount of the solvent may be more than 0 mass %, 1 mass % or more, 2 mass % or more, or 3 mass % or more and may be 50 mass % or less, 20 mass % or less, 10 mass % or less, 6 mass % or less, or 5 mass % or less. When the content of water in the solvent is equal to or larger than the lower limit value, it is possible to improve the solubility and dispersibility of flavonoid glycosides in the solvent and it is possible to further promote decomposition of flavonoid glycosides. On the other hand, when the content of water exceeds the upper limit value, since the content of the alcohol in the solvent tends to decrease relatively and an effect of promoting decomposition of flavonoid glycosides tends to decrease, the content of water is preferably equal to or less than the upper limit value.

The amount of the solvent is not particularly limited as long as it is an amount sufficient for performing the heat treatment, and the solid content of the raw material with respect to 100 parts by mass of the solvent may be 1 part by mass or more, 2 parts by mass or more, 4 parts by mass or more, or 5 mass or more and may be 100 parts by mass or less, 33 parts by mass or less, 25 parts by mass or less, 18 parts by mass or less, or 11 parts by mass or less. In addition, the content of the solid content of the raw material in the reaction solution (concentration of the raw material) with respect to a total amount of the reaction solution may be 1.0 mass % or more, 2.0 mass % or more, 3.8 mass % or more, or 4.8 mass % or more and may be 50 mass % or less, 25 mass % or less, 20 mass % or less, 15 mass % or less, or 10 mass % or less. When the amount of the solvent or the concentration of the raw material is within the above range, it is possible to efficiently decompose flavonoid glycosides. In addition, if the ratio of the solid content of the raw material with respect to the solvent or the concentration of the raw material is equal to or less than the upper limit value, the yield of flavonoids tends to improve when flavonoids are extracted from a decomposition product obtained by the decomposition method of the present embodiment.

The reaction solution preferably does not contain an acid. In particular, the reaction solution preferably does not contain an inorganic acid such as hydrochloric acid, sulfuric acid, and nitric acid. When the reaction solution contains an inorganic acid, this is not preferable because highly toxic organochlorine compounds, organic nitrogen-based compounds, and organic sulfur-based compounds are easily produced by the heat treatment in the sealed container. In addition, when the reaction solution contains an inorganic acid, there is a risk of the acid remaining in the product and there is also a problem of high cost because a process of sufficiently removing an inorganic acid is required to prevent the acid from remaining in the product. The content of the inorganic acids in the reaction solution with respect to a total amount of the reaction solution is preferably 1 mass % or less, 0.1 mass % or less, or 0.01 mass % or less. Here, the incorporation of an organic acid derived from a living body such as citric acid, acetic acid, aspartic acid, amino acid, and nucleic acid is not particularly limited. In this specification, the total amount of the reaction solution means a total amount of the reaction solution before the heat treatment is performed (before heating and pressurizing are performed in the sealed container).

The content of flavonoid glycosides in the reaction solution with respect to a total amount of the reaction solution may be 0.005 mass % or more, 0.01 mass % or more, 0.02 mass % or more, or 0.03 mass % or more and may be 10 mass % or less, 5 mass % or less, 3 mass % or less, 1 mass % or less, 0.9 mass % or less, 0.5 mass % or less, 0.3 mass % or less, or 0.1 mass % or less. When the content is equal to or larger than the lower limit value, the flavonoid production efficiency tends to improve. On the other hand, when the content is equal to or less than the upper limit value, the yield of flavonoids tends to improve when flavonoids are extracted from a decomposition product obtained by the decomposition method of the present embodiment. This is thought to be caused by the fact that, if the concentration of flavonoid glycosides in the reaction solution is high, when sugars separated from the flavonoid glycosides are polymerized (caramelization reaction) and amino acids are present in the reaction solution, the sugars and the amino acids are easily polymerized (Maillard reaction). Polymers of sugars (caramelization reaction product and Maillard reaction product) are unlikely to be dissolve in water or an alcohol. Then, it is speculated that decomposed flavonoids are incorporated into the sugar polymers and extraction of flavonoids is hindered, which causes decrease in the yield of flavonoids.

Reaction conditions for the heat treatment are not particularly limited, and may be, for example, 110 to 300° C. for 0.5 to 20 hours. The reaction temperature is preferably 120 to 190° C., and more preferably 140 to 185° C. When the reaction temperature is 110° C. or higher, the reaction tends to occur more favorably, and when the reaction temperature is 300° C. or lower, the raw material and the flavonoid are unlikely to be carbonized, and the yield tends to be further improved. The reaction time is preferably 0.5 to 20 hours and more preferably 1 to 10 hours. When the reaction time is 0.5 hours or longer, the reaction is more likely to proceed, and when the reaction time is 20 hours or shorter, it is easier to achieve a balance between the progress of the reaction and the cost.

If a mixed solvent is used when the heat treatment, the reaction temperature may be a temperature exceeding a temperature (that is, a boiling point in consideration of boiling point rise and the like) at which the alcohol in the mixed solvent evaporates at room temperature in the mixed solvent state. When the solvent contains a plurality of types of alcohols, the reaction temperature can be set based on the alcohol with the lowest boiling point. Here, in order to efficiently perform decomposition of flavonoid glycosides, the reaction temperature is preferably a temperature exceeding a temperature at which, in a solvent composed of a plurality of types of alcohols or in a mixed solvent of an alcohol and another solvent, the solvent with the highest boiling point evaporates at room temperature.

In order to improve the yield of flavonoids, the heat treatment is preferably performed under conditions of a low temperature (for example, lower than 200° C.) for a long time (for example, 1 hour or longer). When the reaction temperature is a high temperature, bumping of the reaction solution is likely to occur during cooling after the reaction, and the reaction solution scatters out of the container containing the reaction solution when bumping occurs, and thus the yield tends to decrease. In addition, when cooling is performed to prevent the occurrence of the above bumping, since a long cooling time is necessary, work efficiency decreases. This problem of long cooling time is a disadvantage particularly when a large amount of flavonoids is produced. In order to address such problems, the heat treatment is preferably performed under conditions of a low temperature for a long time. Even if the heat treatment is performed at a low temperature, sufficient flavonoid glycosides can be decomposed into flavonoids by prolonging the reaction time. In addition, when the heat treatment is performed under conditions of a low temperature for a long time, it is possible to shorten the entire process time including the cooling time after the heat treatment compared with when the heat treatment is performed under conditions of a high temperature for a short time.

The pressure in the container during the heat treatment may be a saturated vapor pressure corresponding to the reaction temperature of an alcohol or a mixed solvent of an alcohol and another solvent, or higher, but the saturated vapor pressure is preferable in consideration of pressure resistance of the device. The pressure in the sealed container during the heat treatment can be, for example, 0.2 to 1.6 MPa.

When the heat treatment is performed under the above conditions, flavonoid glycosides can be efficiently decomposed into flavonoids (more specifically, flavonoids and sugars).

(Method for Producing Flavonoids)

A method for producing flavonoids according to the present embodiment includes a decomposition process in which flavonoid glycosides are decomposed and an extraction process in which flavonoids are extracted from a decomposition product obtained in the decomposition process. The decomposition process is a process in which flavonoid glycosides are decomposed by the above method for decomposing flavonoid glycosides according to the present embodiment.

In the extraction process, flavonoids are extracted from a decomposition product obtained in the decomposition process. The decomposition product includes sugars, flavonoid glycosides remaining without decomposition, water-soluble and poorly soluble celluloses and their decomposition products, and the like in addition to the flavonoids. Here, flavonoids are hydrophobic, but sugars, flavonoid glycosides, water-soluble celluloses and their decomposition products are hydrophilic. Therefore, flavonoids are contained in a high concentration in components that are insoluble in water after the heat treatment, and flavonoids can be concentrated by separating the aqueous solution and the water-insoluble content after the heat treatment. In addition, when the water-insoluble content is additionally dissolved in a solvent in which flavonoids are dissolved, for example, ethanol, ethyl acetate, hexane, toluene, or the like, and a mixed solvent thereof, and insoluble components are removed by filtration or the like, it is possible to further extract and purify the flavonoids. Then, flavonoids with a high concentration can be obtained by drying the filtrate.

According to the method, it is possible to efficiently produce flavonoids in a high yield. The flavonoids produced by the production method of the present embodiment may be polymethoxyflavone, sudachitin and/or demethoxysudachitin. The production method of the present embodiment is preferable for producing polymethoxyflavone, particularly, sudachitin and demethoxysudachitin, and the yield thereof can be greatly improved.

EXAMPLES

While the present invention will be described below in more detail with reference to examples and comparative examples, the present invention is not limited to the following examples.

Example 1

2 g of sudachi peel extract powder (commercially available from Ikeda Yakusou Co., Ltd.) containing 1,000 ppm by mass of sudachitin, 1,500 ppm by mass of demethoxysudachitin, 8,000 ppm by mass of glycoside-derived sudachitin, and 3,000 ppm by mass of glycoside-derived demethoxysudachitin was dissolved/dispersed in 50 g of ethanol (special grade, purity 99.5%, commercially available from Wako Pure Chemical Industries, Ltd.) as a solvent, and put into a Teflon (registered trademark) container with a capacity of 100 ml, and additionally, the Teflon (registered trademark) container was placed in a stainless steel pressure-resistant container, and the pressure-resistant container was sealed. In the sealed pressure-resistant container, while stirring the solution in the Teflon (registered trademark) container using a magnetic stirrer at a rotational speed of 600 rpm, heat treatment was performed by a heater so that the temperature of the solution became 180° C. After the temperature reached 180° C., the heat treatment was performed at 180° C. for 60 minutes while continuing stirring. Then, heating and stirring were stopped and the sample was naturally cooled to room temperature (25° C.). Here, the highest reachable temperature during the heat treatment was 181° C. After cooling, the solution and solid content in the Teflon (registered trademark) container were taken out with a beaker and vacuum-dried using a diaphragm pump while heating at 60° C. to obtain 1.9 g of a powdered glycoside decomposition sample 1.

Example 2

1.8 g of a powdered glycoside decomposition sample 2 was obtained in the same manner as in Example 1 except that 50 g of methanol (special grade, purity 99.5%, commercially available from Wako Pure Chemical Industries, Ltd.) was used as the solvent.

Example 3

The heat treatment was performed at 180° C. for 60 minutes in the same manner as in Example 1 except that 50 g of glycerin (commercially available from Wako Pure Chemical Industries, Ltd.) was used as the solvent. Then, heating and stirring were stopped and the sample was naturally cooled to room temperature (25° C.). After cooling, 1 L of water was added to the solution and the mixture was stirred to precipitate a glycoside decomposition product containing sudachitin and demethoxysudachitin. This solution was filtered with a 0.2 µm PTFE mesh under a reduced pressure using a diaphragm pump, and the precipitated solid content was separated to obtain a powdered glycoside decomposition sample 3.

Example 4

1.85 g of a powdered glycoside decomposition sample 4 was obtained in the same manner as in Example 1 except that 50 g of a mixed solvent of water/ethanol (mass ratio 5/95) was used as the solvent.

Example 5

1.85 g of a powdered glycoside decomposition sample 5 was obtained in the same manner as in Example 1 except that 50 g of a mixed solvent of water/ethanol (mass ratio 20/80) was used as the solvent.

Example 6

1.7 g of a powdered glycoside decomposition sample 6 was obtained in the same manner as in Example 1 except that 50 g of a mixed solvent of water/ethanol (mass ratio 50/50) was used as the solvent.

Example 7

1.85 g of a powdered glycoside decomposition sample 7 was obtained in the same manner as in Example 1 except that 50 g of a mixed solvent of water/ethanol (mass ratio 80/20) was used as the solvent.

Example 8

1.85 g of a powdered glycoside decomposition sample 8 was obtained in the same manner as in Example 1 except that 50 g of a mixed solvent of water/ethanol (mass ratio 95/5) was used as the solvent.

Examples 9 to 11

Powdered glycoside decomposition samples 9 (1.9 g), 10 (1.85 g), and 11 (1.8 g) were obtained in the same manner in Example 1 except that the temperature of water during the heat treatment was set to 160° C. (Example 9), 140° C. (Example 10), and 120° C. (Example 11).

Examples 12 to 15

Powdered glycoside decomposition samples 12 (1.75 g), 13 (1.8 g), 14 (1.8 g), and 15 (1.8 g) were obtained in the same manner as in Example 1 except that the reaction time during the heat treatment was set to 600 minutes (10 hours) and the temperature during the treatment was set to 120° C. (Example 12), 140° C. (Example 13), 160° C. (Example 14), and 180° C. (Example 15).

Comparative Example 1

2 g of the same sudachi peel extract powder (commercially available from Ikeda Yakusou Co., Ltd.) used in Example 1 was used as a sample of Comparative Example 1.

Comparative Example 2

2 g of the same sudachi peel extract powder (commercially available from Ikeda Yakusou Co., Ltd.) used in Example 1 was put into a heat-resistant container, and a lid with an aluminum foil having a hole of about φ3 mm was used so that powder did not scatter with hot air, and a heat treatment was performed in an oven at 180° C. for 1 hour to obtain 1.65 g of a sudachi peel extract powder heat treatment sample.

Reference Example 1

2 g of the same sudachi peel extract powder (commercially available from Ikeda Yakusou Co., Ltd.) used in Example 1 was dissolved/dispersed in 50 g of 1 N hydrochloric acid and heated at 80° C. for 1 hour while stirring at a rotational speed of 600 rpm using a magnetic stirrer, heating and stirring were then stopped and the sample was naturally cooled to room temperature (25° C.). The reaction solution after cooling was neutralized in a 1 N sodium hydroxide aqueous solution and vacuum-dried using a diaphragm pump while heating at 60° C. to obtain 1.8 g of a powdered glycoside hydrochloric acid decomposition sample.

<Measurement of Concentration of Sudachitin and Concentration of Demethoxysudachitin>

The concentration of sudachitin and the concentration of demethoxysudachitin of the samples obtained in the examples, comparative examples and reference examples were measured by the following method. First, 0.1 g of the sample was dissolved/dispersed in ethanol so that the dilution factor was 500, and filtered with a PTFE filter having a pore size of 0.1 μm to obtain an ethanol solution. Components of this ethanol solution were analyzed by high performance liquid chromatography (HPLC). Calibration curves were created using a commercially available sudachitin standard purified sample and a commercially available demethoxysudachitin standard purified sample as standard substances, and used to roughly estimate the concentration of sudachitin and the concentration of demethoxysudachitin in the sample. "Chromaster" (commercially available from Hitachi High-Tech Corporation) was used as the HPLC device. The results are summarized in Table 1.

TABLE 1

| | Sample | Solvent | Heat treatment temperature (° C.) | Heat treatment time (hours) | Sudachitin concentration (ppm by mass) | Demethoxysudachitin concentration (ppm by mass) |
| --- | --- | --- | --- | --- | --- | --- |
| Example 1 | Glycoside decomposition sample 1 | Ethanol | 180 | 1 | 10100 | 3900 |
| Example 2 | Glycoside decomposition sample 2 | Methanol | 180 | 1 | 5700 | 2100 |
| Example 3 | Glycoside decomposition sample 3 | Glycerin | 180 | 1 | 5800 | 2800 |
| Example 4 | Glycoside decomposition sample 4 | Water/Ethanol (5/95) | 180 | 1 | 13000 | 4000 |
| Example 5 | Glycoside decomposition sample 5 | Water/Ethanol (20/80) | 180 | 1 | 5200 | 3200 |
| Example 6 | Glycoside decomposition sample 6 | Water/Ethanol (50/50) | 180 | 1 | 5500 | 3300 |
| Example 7 | Glycoside decomposition sample 7 | Water/Ethanol (80/20) | 180 | 1 | 5900 | 3500 |
| Example 8 | Glycoside decomposition sample 8 | Water/Ethanol (95/5) | 180 | 1 | 5300 | 3000 |
| Example 9 | Glycoside decomposition sample 9 | Ethanol | 160 | 1 | 5000 | 2900 |
| Example 10 | Glycoside decomposition sample 10 | Ethanol | 140 | 1 | 3200 | 2400 |
| Example 11 | Glycoside decomposition sample 11 | Ethanol | 120 | 1 | 2100 | 2000 |
| Example 12 | Glycoside decomposition sample 12 | Ethanol | 120 | 10 | 3000 | 2200 |
| Example 13 | Glycoside decomposition sample 13 | Ethanol | 140 | 10 | 5000 | 2700 |
| Example 14 | Glycoside decomposition sample 14 | Ethanol | 160 | 10 | 8300 | 3000 |
| Example 15 | Glycoside decomposition sample 15 | Ethanol | 180 | 10 | 11000 | 3500 |
| Comparative Example 1 | Sudachi peel extract powder | — | — | — | 1000 | 1100 |
| Comparative Example 2 | Extract powder heat treatment sample | — | — | — | 600 | 200 |
| Reference Example 1 | Glycoside hydrochloric acid decomposition sample | — | — | — | 9500 | 1700 |

As shown in Table 1, it can be understood that, in all of Examples 1 to 15, compared with Comparative Examples 1 and 2, the concentration of sudachitin and the concentration of demethoxysudachitin increased, and sudachitin glycoside and demethoxysudachitin glycoside were decomposed to newly generate sudachitin and demethoxysudachitin as polymethoxyflavone, and the yield of sudachitin and demethoxysudachitin could be improved. In addition, it can be understood that, in Examples 1 to 15, without using hydrochloric acid as in Reference Example 1, the concentration of sudachitin and the concentration of demethoxysudachitin could be improved, and the concentration of sudachitin and the concentration of demethoxysudachitin could be improved compared with when hydrochloric acid had been used depending on conditions.

What is claimed is:

1. A method for decomposing flavonoid glycosides, comprising
    performing a heat treatment on a raw material containing flavonoid glycosides in a sealed container in the presence of an alcohol at a temperature exceeding a boiling point of the alcohol at atmospheric pressure to decompose the flavonoid glycosides into flavonoids, wherein the heat treatment is performed in the temperature range of 180 to 300° C. for 0.5 to 10 hours, and the flavonoid glycosides include sudachitin glycoside and/or demethoxysudachitin glycoside.

2. The method for decomposing flavonoid glycosides according to claim 1, wherein the heat treatment is performed by heating a reaction solution containing the raw material and the alcohol in the sealed container,
    wherein the content of the flavonoid glycosides in the reaction solution with respect to a total amount of the reaction solution is 0.01 to 3 mass %.

3. The method for decomposing flavonoid glycosides according to claim 1, wherein the heat treatment is performed by heating a reaction solution containing the raw material and the alcohol in the sealed container,
    wherein the content of an inorganic acid in the reaction solution with respect to a total amount of the reaction solution is 1 mass % or less.

4. The method for decomposing flavonoid glycosides according to claim 1,
    wherein the heat treatment is performed in the presence of a solvent containing the alcohol and water.

5. The method for decomposing flavonoid glycosides according to claim 4,
    wherein the content of the alcohol in the solvent with respect to a total amount of the solvent is 90 mass % or more.

6. The method for decomposing flavonoid glycosides according to claim 4,
    wherein the content of water in the solvent with respect to a total amount of the solvent is 10 mass % or less.

7. The method for decomposing flavonoid glycosides according to claim 1,
    wherein the raw material further contains flavonoids.

8. The method for decomposing flavonoid glycosides according to claim 1,
    wherein the raw material is a dry powder obtained from citrus fruits or a pericarp of citrus fruits.

9. A method for producing flavonoids, comprising:
    a decomposition process in which the flavonoid glycosides are decomposed by the method for decomposing flavonoid glycosides according to claim 1; and
    an extraction process in which flavonoids are extracted from a decomposition product obtained in the decomposition process.

* * * * *

UNITED STATES PATENT AND TRADEMARK OFFICE
CERTIFICATE OF CORRECTION

Page 1 of 1

PATENT NO. : 12,195,436 B2
APPLICATION NO. : 17/262207
DATED : January 14, 2025
INVENTOR(S) : Motohiro Arifuku et al.

It is certified that error appears in the above-identified patent and that said Letters Patent is hereby corrected as shown below:

On the Title Page

Insert item (30) Foreign Application Priority Data:
--Jul. 27, 2018 (JP).............................PCT/JP2018/028287--

Signed and Sealed this
First Day of April, 2025

Coke Morgan Stewart
*Acting Director of the United States Patent and Trademark Office*